US010578551B2

(12) United States Patent
Campbell et al.

(10) Patent No.: US 10,578,551 B2
(45) Date of Patent: Mar. 3, 2020

(54) IN-SITU DETECTION OF HOLLOW GLASS FIBER FORMATION

(71) Applicant: International Business Machines Corporation, Armonk, NY (US)

(72) Inventors: Eric J. Campbell, Rochester, MN (US); Bruce J. Chamberlin, Vestal, NY (US); Sarah K. Czaplewski, Rochester, MN (US); Scott B. King, Rochester, MN (US); Joseph Kuczynski, North Port, FL (US)

(73) Assignee: International Business Machines Corporation, Armonk, NY (US)

( * ) Notice: Subject to any disclaimer, the term of this patent is extended or adjusted under 35 U.S.C. 154(b) by 204 days.

(21) Appl. No.: 15/809,075

(22) Filed: Nov. 10, 2017

(65) Prior Publication Data

US 2018/0106719 A1   Apr. 19, 2018

Related U.S. Application Data

(63) Continuation of application No. 15/297,197, filed on Oct. 19, 2016, now Pat. No. 9,863,875.

(51) Int. Cl.
*G01R 31/28* (2006.01)
*G01N 21/41* (2006.01)
(Continued)

(52) U.S. Cl.
CPC ........... *G01N 21/412* (2013.01); *G01N 21/84* (2013.01); *H05K 1/0306* (2013.01);
(Continued)

(58) Field of Classification Search
CPC ..... C03C 25/40; C03C 25/28; C03C 25/1095; H05K 1/0306; H05K 1/0366; H05K 1/038; B05D 3/002
See application file for complete search history.

(56) References Cited

U.S. PATENT DOCUMENTS 4,021,217 A   5/1977  Bondybey et al.
4,174,198 A   11/1979 Kinoshita
(Continued)

FOREIGN PATENT DOCUMENTS

GB    619769 A     3/1949
JP    55051731 A   4/1980
(Continued)

OTHER PUBLICATIONS

Appendix P; List of IBM Patent or Applications Treated as Related, Nov. 10, 2017, 2 pages.
(Continued)

*Primary Examiner* — Paul D Kim
(74) *Attorney, Agent, or Firm* — Nolan M. Lawrence

(57) ABSTRACT

A process of in-situ detection of hollow fiber formation includes immersing a plurality of individual glass fibers in an index-matching material. The index-matching material has a first refractive index that substantially matches a second refractive index of the glass fibers. The process also includes exposing the individual glass fibers to a light source during immersion in the index-matching material. The process further includes utilizing one or more optical components to collect optical data for the individual glass fibers during immersion in the index-matching material. The process also includes determining, based on the optical data, that a particular glass fiber of the plurality of individual glass fibers includes a hollow fiber.

20 Claims, 5 Drawing Sheets

(51) Int. Cl.
*G01N 21/84* (2006.01)
*H05K 3/00* (2006.01)
*H05K 1/03* (2006.01)

(52) U.S. Cl.
CPC .... *H05K 3/0011* (2013.01); *G01N 2021/8411* (2013.01); *H05K 2203/163* (2013.01)

(56) References Cited

U.S. PATENT DOCUMENTS

| | | | |
|---|---|---|---|
| 4,924,087 | A | 5/1990 | Bailey et al. |
| 5,185,636 | A | 2/1993 | Button et al. |
| 5,330,548 | A | 7/1994 | Danzuka et al. |
| 5,352,258 | A | 10/1994 | DeGreve et al. |
| 5,436,719 | A | 7/1995 | Doles et al. |
| 5,469,252 | A | 11/1995 | Doles et al. |
| 5,490,931 | A * | 2/1996 | Chung ............... B01D 69/08 210/500.23 |
| 5,776,222 | A | 7/1998 | Kopylov et al. |
| 5,880,825 | A | 3/1999 | Jakobsen et al. |
| 6,212,936 | B1 | 4/2001 | Meisberger |
| 6,313,909 | B1 | 11/2001 | Frazee, Jr. et al. |
| 6,436,319 | B1 * | 8/2002 | Sun ................... B01D 67/0025 264/178 F |
| 6,478,913 | B1 | 11/2002 | Dunleavy et al. |
| 7,940,382 | B2 | 5/2011 | Ikeda et al. |
| 8,689,588 | B2 | 4/2014 | Hirayama et al. |
| 8,974,888 | B2 | 3/2015 | Balcome et al. |
| 9,360,618 | B2 * | 6/2016 | Feder ................. G02B 6/02123 |
| 2004/0096169 | A1 * | 5/2004 | Sone ................... B01J 19/0046 385/115 |
| 2008/0221814 | A1 | 9/2008 | Trainer |
| 2009/0202853 | A1 * | 8/2009 | Magno ..................... D01F 6/04 428/523 |
| 2010/0215948 | A1 * | 8/2010 | Kissounko ............. C03C 25/26 428/327 |
| 2012/0167633 | A1 | 7/2012 | Hirayama et al. |
| 2014/0167633 | A1 | 6/2014 | Zhang |
| 2015/0034755 | A1 | 2/2015 | Kuramata et al. |
| 2015/0085276 | A1 | 3/2015 | Uchino et al. |
| 2016/0207814 | A1 | 7/2016 | Demott et al. |
| 2017/0021548 | A1 | 1/2017 | Czaplewski et al. |
| 2017/0022084 | A1 | 1/2017 | Czaplewski et al. |

FOREIGN PATENT DOCUMENTS

| | | |
|---|---|---|
| JP | 07229813 A | 8/1995 |
| JP | 08208264 A | 8/1996 |
| JP | 08319131 A | 12/1996 |
| JP | 2003192373 A | 7/2003 |
| KR | 1020030067610 A | 8/2003 |
| WO | WO-2008018997 A2 | 2/2008 |

OTHER PUBLICATIONS

Anonymous, *Method for Detection of Hollow Glass Fibers*, An IP.com Prior Art Database Technical Disclosure, Sep. 20, 2011, 3 pages, ip.com (online), IP.com No. IPCOM000211112D.

Campbell et al., *In-Situ Detection of Hollow Glass Fiber Formation*, IBM, U.S. Appl. No. 15/297,197, filed Oct. 19, 2016, 20 pages.

Campbell et al., *In-Situ Detection of Hollow Glass Fiber Formation*, IBM, U.S. Appl. No. 15/705,479, filed Sep. 15, 2017, 20 pages.

Liu et al., *Joint transform correlator for the detection of defects in optical fibers*, Optical Engineering, vol. 37, No. 5, May 1998, 7 pages, Society of Photo-Optical Instrumentation Engineers, spiedigitallibrary.org (online), <http://dx.doi.org/10.1117/1.601662>.

* cited by examiner

IN-SITU DETECTION OF HOLLOW GLASS FIBER FORMATION

CROSS-REFERENCE TO RELATED APPLICATION

This application is a continuation application of and claims priority from U.S. patent application Ser. No. 15/297,197, filed on Oct. 19, 2016, now U.S. Pat. No. 9,863,875.

BACKGROUND

Printed circuit boards typically include a mat of woven glass fibers within a cured resin substrate. The glass fibers provide structural reinforcement for the resin. The glass fibers are formed by extruding molten glass. Occasionally, a bubble in the molten glass is carried into the extrusion process. In such cases, the bubble can be contained in a formed thread in an elongated form. As a result, the thread includes a hollow region.

If a hollow thread is used in the manufacture of a printed circuit board, the hollow thread could cause a circuit failure, such as a short circuit or an open circuit. For example, holes or vias are often drilled through a printed circuit board. If such a hole is drilled through a hollow thread, a conductive circuit material could travel through the hollow portion of the thread, forming a conductive anodic filament (CAF) that may cause an electrical failure in the printed circuit board. As the density of circuit elements on printed circuit boards increases, the likelihood that a hollow thread will cause a circuit failure also increases. Thus, reducing or eliminating the presence of hollow threads in printed circuit boards is important to reduce the number of faulty circuit boards.

Hollow fiber detection is difficult once the glass fibers are formed into glass cloth. The glass cloth is typically stored in long rolls (e.g., 2 kilometer rolls), of which only a small portion (e.g., the first 10 centimeters) can be feasibly tested for the presence of hollow fibers. Then, the hollow fiber count for the small sampled portion may be extrapolated onto the entire roll of glass cloth. Such sampling methods do not offer a reliable nor reasonable measure of an amount of hollow fibers that are present in a particular sheet of pre-impregnated (prepreg) material that is used to form a printed circuit board.

SUMMARY

According to an embodiment, a process of in-situ detection of hollow fiber formation is disclosed. The process includes immersing a plurality of individual glass fibers in an index-matching material. The index-matching material has a refractive index that substantially matches the refractive index of the glass fibers. The process also includes exposing the individual glass fibers to a light source during immersion in the index-matching material. The process further includes utilizing one or more optical components to collect optical data for the individual glass fibers during immersion in the index-matching material. The process also includes determining, based on the optical data, that a particular glass fiber of the plurality of individual glass fibers includes a hollow fiber.

According to another embodiment, an apparatus for in-situ detection of hollow fiber formation is disclosed. The apparatus includes an immersion component to immerse a plurality of individual glass fibers in an index-matching material. The index-matching material has a refractive index that substantially matches the refractive index of the glass fibers. The apparatus includes a light source to expose the individual glass fibers to light during immersion in the index-matching material. The apparatus also includes one or more optical components to collect optical data for the individual glass fibers during immersion in the index-matching material. The apparatus further includes a hollow fiber identification component to determine, based on the optical data, that a particular glass fiber of the plurality of individual glass fibers includes a hollow portion.

According to another embodiment, a process is disclosed that includes receiving a woven glass fiber cloth from a glass cloth manufacturer. The process includes determining, based on glass fiber defect data received from the glass cloth manufacturer, a location in the woven glass fiber cloth that includes a hollow glass fiber. The process also includes selectively removing a portion of the woven glass fiber cloth that is associated with the location to form a second woven glass fiber cloth having the hollow glass fiber removed. The process further includes utilizing the second woven glass fiber cloth having the hollow glass fiber removed to form a pre-impregnated (prepreg) material, and utilizing the prepreg material for printed circuit board manufacturing.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

Figure 1:
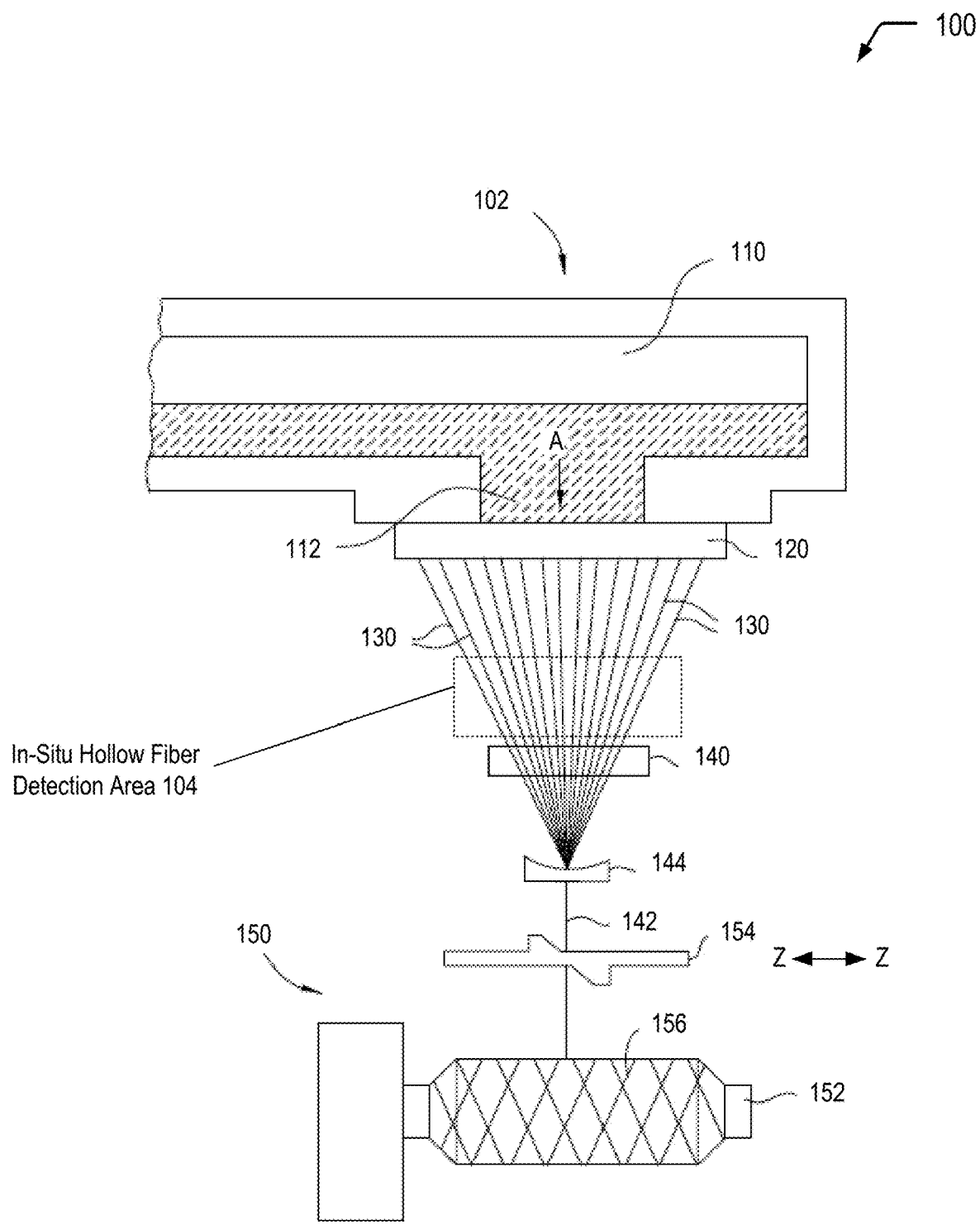
FIG. 1 is a diagram depicting a system for in-situ detection of hollow fiber formation, according to one embodiment.

The present disclosure describes in-situ detection of hollow glass fiber formation. In the present disclosure, hollow filaments are identified before the glass fibers are woven into a glass cloth (e.g., for use in formation of a printed circuit board). Prior to bundling of individual glass fibers (after the individual glass fibers leave the furnace), the individual glass fibers may be immersed in a material having an index of refraction that matches the index of refraction of the glass. While the individual glass fibers are immersed in the index-matching material, a light source may be used to illuminate hollow filaments that may be present in the individual glass fibers.

In the event that an individual glass fiber includes a hollow portion, the index of refraction of the air inside the glass fiber will be different than that of the glass and the index-matching material. The index of refraction of the immersion liquid matching that of the glass results in light refraction only in locations where air is trapped in the glass fiber. Data associated with the locations of the hollow filaments may be stored and subsequently utilized for removal of sections of a woven glass cloth that include the hollow filaments. Selective removal of defective sections of the woven glass cloth may reduce a likelihood of circuit failure that may be associated with hollow filaments.

As described further herein, glass fibers are typically manufactured via an extrusion process. First, the appropriate dry mixture of silicas, limestone, clay, and boric acid is melted in a furnace. Once this molten glass mixture is homogenous, the mixture is allowed to flow into a forehearth and is then passed through a bushing with tiny nozzles to create fibers. The fibers are then sprayed with water to cool them, and a sizing material is applied to protect the fibers during subsequent processing. The fibers are then bundled into yarns and collected on a mandrel before being woven into a glass cloth. Hollow fibers may be formed when gas bubbles are trapped inside the molten glass. These bubbles are often caused by entrapment of air or the release of gas during decomposition of the water, carbonates, and organic matter in the raw materials. If a bubble remains trapped and passes through the bushing, the bubble can be drawn out to create a capillary inside the glass fiber.

In the present disclosure, after the molten glass is extruded from the bushing, glass fibers enter a cooling pathway (also referred to herein as an "in-situ hollow fiber detection area") prior to sizing application. Along the cooling pathway, the fibers are submerged into a liquid with a refractive index that substantially matches the refractive index of the glass, such as oil of wintergreen. A light source shines onto the fibers. If a hollow fiber is present, the light will refract off of the hollow fiber interface. A camera is employed to detect the refracted light from the hollow fibers. By detecting the hollow fibers, a glass manufacturer can track the distribution and length of the hollow fibers across their furnaces. This data can be used to track distributions of hollow fibers in a bobbin and to provide insight into the glass furnace performance by providing data of hollow filament formation for each bushing. This data can be used in future furnace designs to mitigate hollow filament formation and growth. Further, by identifying the locations of the hollow filaments, the portions of a woven glass cloth that include the hollow filaments may be removed in order to reduce the likelihood of CAF formation in a printed circuit board associated with the presence of such hollow filaments. Alternatively, woven glass cloths may be "graded" for use in applications where the presence of hollow glass filaments is not as important as in the context of printed circuit boards.

Referring to FIG. 1, a diagram 100 illustrates a system of in-situ detection of hollow glass fiber formation. In the embodiment depicted in FIG. 1, a portion of an apparatus 102 for forming glass threads from a molten glass source is illustrated. As illustrated and further described herein with respect to FIGS. 2 and 3, the apparatus 102 of FIG. 1 includes an in-situ hollow fiber detection area 104 where individual glass fibers may be examined to determine whether the individual glass fibers include hollow portions.

In the embodiment depicted in FIG. 1, selected portions of the apparatus 102 are omitted for ease of illustration purposes only. The apparatus 102 starts with raw materials, such as a dry mixture of silicas, limestone, clay, and boric acid. The raw materials pass-through measuring devices (not shown) that distribute the raw materials in the proper amounts or proportions. The raw materials then pass through a mixer (not shown), and the mixed raw materials are then dropped into a furnace. The furnace melts the raw materials to a temperature of between 1370° C. and 1540° C. to form a molten glass mixture. The molten glass mixture flows into a refiner (not shown) where the molten glass mixture cools to a temperature of between 1340° C. and 1425° C. The molten glass mixture homogenizes as it flows into the refiner. Additionally, gas bubbles in the molten glass mixture (e.g., caused by entrapment of air or the release of gas during decomposition of water, carbonates, and/or organic matter in the raw materials) travel to the surface of the molten glass mixture refiner. After the refiner, the molten glass mixture passes into a forehearth 110 where the molten glass mixture cools to a temperature of between 1260° C. and 1371° C. In the forehearth 110, any remaining bubbles may float to the surface of the molten glass mixture, resulting in a molten glass mixture 112 that is ready to be extruded into glass threads.

The illustrated portion of the apparatus 102 includes one bushing 120 arranged under the forehearth 110. In various embodiments, the apparatus 102 can include an alternative number of bushings (e.g., three bushings). The molten glass 112 travels in the direction of arrow A into the bushing 120. The bushing 120 includes nozzles (not shown) through which the molten glass can be extruded as individual glass threads 130.

Optionally, the individual glass threads 130 pass through a sizer 140, which finalizes the diameter of the individual glass threads 130. The individual glass threads 130 can be formed into a glass strand 142 by a strand former 144, which braids, twists, and/or otherwise combines the individual glass threads 130. The glass strand 142 can then be wound onto winders 150. The winders 150 include a rotating spool 152. A traversing mechanism 154 can move in the direction of arrows Z to laterally distribute the glass strand 142 about the spool 152. For example, the glass strand 142 can be arranged on the spool 152 in a crisscross or woven pattern 156. The process of forming the glass strand 142 may be performed in a continuous manner, meaning that a spool of the glass strand is formed on the spool 152 until the spool 152 is full or otherwise reaches a predetermined size.

As discussed above, occasionally, a gas bubble can remain entrapped in the molten glass mixture 112. When the bubble reaches one of the nozzles in the bushing 120, the gas bubble can be extruded into an elongated hollow within an individual glass thread 130. As discussed above, such an elongated hollow in the thread 130 could cause an electrical failure of a printed circuit board.

The apparatus 102 includes an in-situ hollow fiber detection area 104 that includes a cooling pathway arranged below the bushing 120 to receive the individual glass threads 130. Along the cooling pathway, the individual glass threads 130 are submerged into a liquid with an index of refraction that matches an index of refraction of the glass. As an illustrative, non-limiting example, the individual glass threads 130 may be submerged into oil of wintergreen. While oil of wintergreen represents the industry standard for identifying hollow fibers for e-glass due to index of refraction matching, it will be appreciated that alternative index-matching materials or combinations of materials may be utilized.

Figure 2:
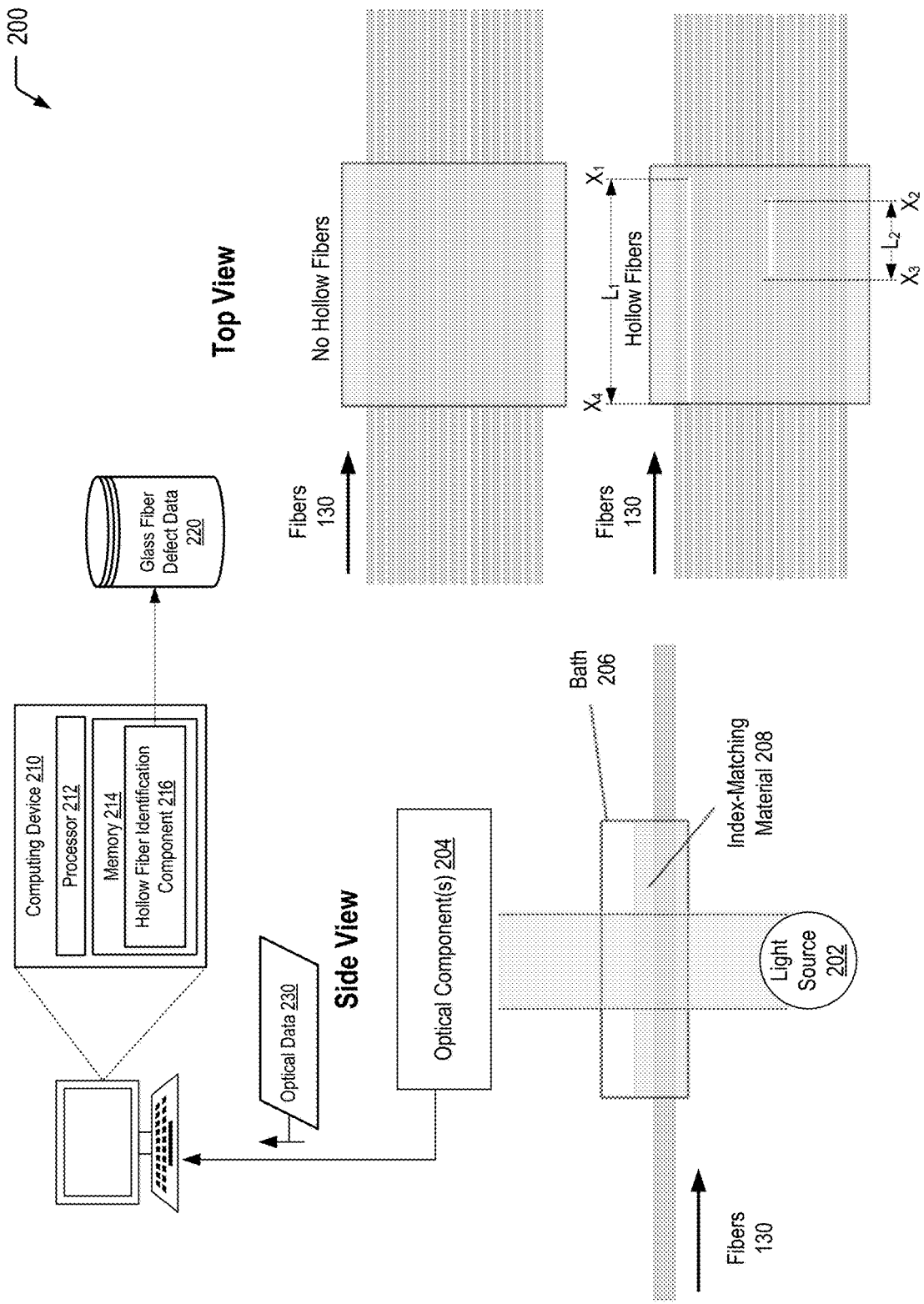
FIG. 2 is a diagram depicting an example configuration for in-situ detection of hollow fiber formation, according to one embodiment.
Figure 3:
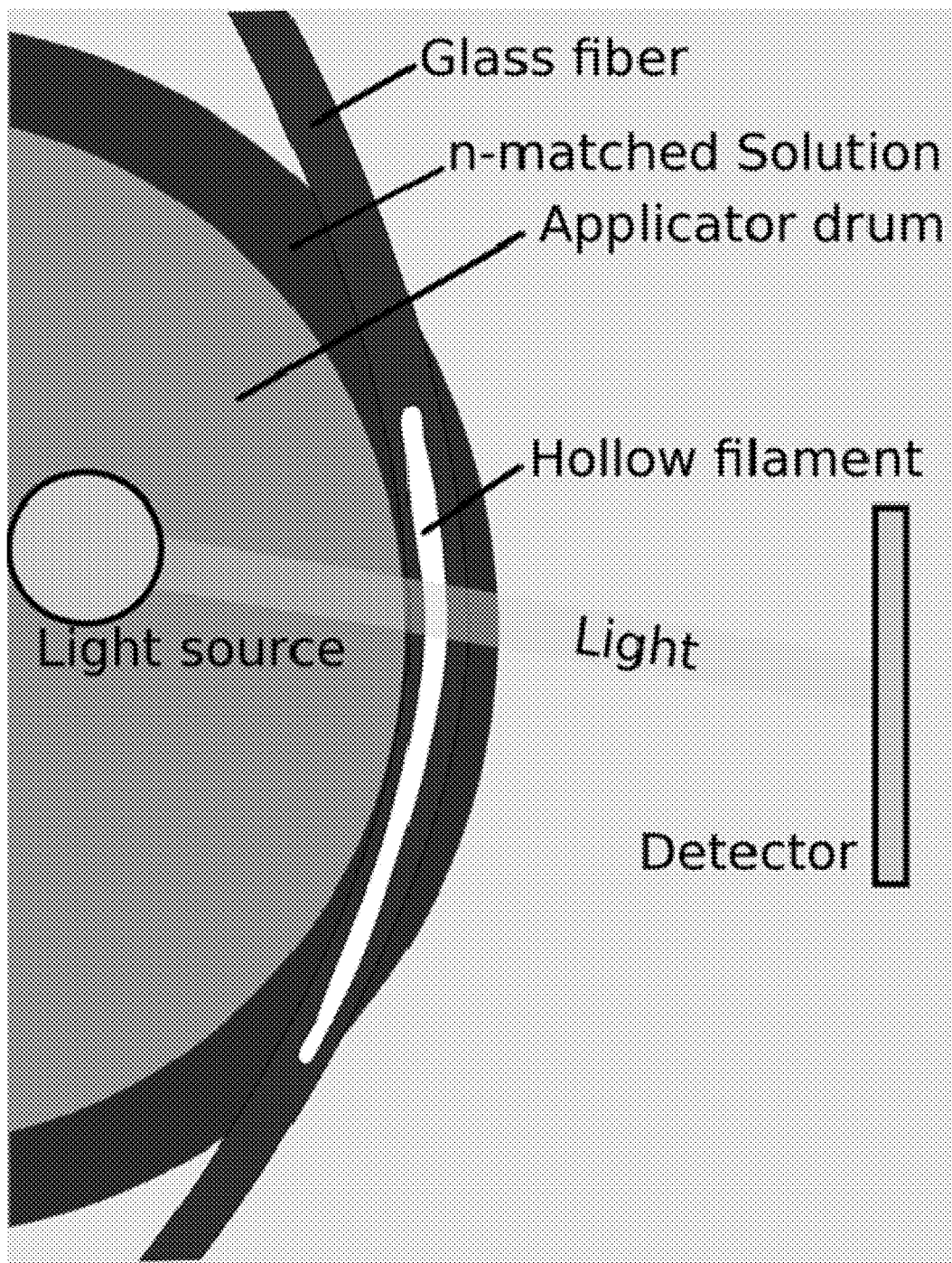
FIG. 3 is a diagram depicting an example configuration for in-situ detection of hollow fiber formation, according to one embodiment.

As illustrated and further described herein with respect to FIGS. 2 and 3, a light source 202 (not shown in FIG. 1) shines onto the glass threads 130. If a hollow fiber is present, the light will refract off of the hollow fiber interface. A camera (or other imaging sensor) is employed to detect the refracted light from the hollow fibers. By detecting the hollow fibers, the glass manufacturer can track the distribution and length of the hollow fibers across their furnaces.

This data can be used to track distributions of hollow fibers in a bobbin and to provide insight into the glass furnace performance by providing data of hollow filament formation for each bushing. This data can be used in future furnace designs to reduce hollow filament formation and growth.

Thus, FIG. 1 illustrates an example of a system of in-situ detection of hollow glass fiber formation. In FIG. 1, hollow filaments are identified before the glass fibers are woven into a glass cloth (e.g., for use in formation of a printed circuit board). As described further herein, data associated with the locations of the hollow filaments may be stored and subsequently utilized for removal of sections of a woven glass cloth that include the hollow filaments. Selective removal of defective sections of the woven glass cloth may reduce a likelihood of circuit failure that may be associated with hollow filaments.

Referring to FIG. 2, a diagram 200 depicts an example configuration for in-situ detection of hollow fiber formation, according to one embodiment. In a particular embodiment, operations described herein with respect to FIG. 2 correspond to operations performed in the in-situ hollow fiber detection area 104 of FIG. 1. In the example of FIG. 2, the individual glass fibers 130 are submerged into a liquid with a refractive index that substantially matches the refractive index of the glass. Alternatively, as illustrated and described further herein with respect to FIG. 3, a drum may be utilized to apply the index-matching liquid to the fibers 130 for optical analysis.

In the side view of FIG. 2, a light source 202 is used to illuminate the individual glass fibers 130 while the glass fibers 130 are immersed in a bath 206 that includes an index-matching material 208. In the event that one or more of the individual glass fibers 130 includes a hollow portion, the index of refraction of the air inside the fiber(s) 130 will be different than that of the glass and the index-matching material 208. The index of refraction of the immersion liquid matches that of the glass, resulting in light scattering exclusively in locations where air is trapped in the glass fiber 130. One or more optical component(s) 204 (e.g., one or more cameras, other optical sensors, etc.) may be used to detect such light scattering.

In the example of FIG. 2, a computing device 210 is communicatively coupled to the optical component(s) 204. The computing device 210 includes a processor 212 and a memory 214 that stores a hollow fiber identification component 216. The computing device 210 is communicatively coupled to a storage device that stores glass fiber defect data 220. The computing device 210 may receive optical data 230 associated with locations of hollow portion(s) of one or more of the glass fibers 130. The hollow fiber identification component 216 may store data associated with the locations of the hollow filaments as the glass fiber defect data 220. As described further herein, the glass fiber defect data 220 may be subsequently utilized for removal of sections of a woven glass cloth that include the hollow filaments. Selective removal of defective sections of the woven glass cloth may reduce a likelihood of circuit failure that may be associated with hollow filaments.

For illustrative purposes, the top view of FIG. 2 shows examples of glass fibers 130 that do not include hollow fibers and glass fibers 130 that do include hollow fibers. The top view in FIG. 2 depicts examples of the type of data that may be stored as the glass fiber defect data 220, for subsequent utilization for identification of locations for defect removal. To illustrate, a first example of a hollow fiber is shown with a starting location (along an X-axis) of $X_1$ and an ending location of $X_4$, having an overall length of $L_1$. A second example of a hollow fiber is shown with a starting location (along the X-axis) of $X_2$ and an ending location of $X_3$, having an overall length of $L_2$. The glass fiber defect data 220 may be utilized to identify selected portions of a woven glass cloth for removal (e.g., for a prepreg material for a printed circuit board).

Thus, FIG. 2 illustrates an example of one configuration for in-situ detection of hollow fiber formation. In the example of FIG. 2, individual glass fibers are submerged into a liquid with a refractive index that substantially matches the refractive index of the glass. In the event that one or more of the individual glass fibers includes a hollow portion, the index of refraction of the air inside the fiber(s) will be different than that of the glass and the index-matching material. The optical component(s) may detect such light scattering, and a computing device may store location data where such light scattering was detected as being associated with hollow fiber defects.

Referring to FIG. 3, a diagram 300 depicts another example configuration for in-situ detection of hollow fiber formation, according to one embodiment. In a particular embodiment, operations described herein with respect to FIG. 3 correspond to operations performed in the in-situ hollow fiber detection area 104 of FIG. 1. In the example of FIG. 3, individual glass fibers are rolled over a drum that has liquid cascading over the drum. Thus, in contrast to FIG. 2, immersion of the individual glass fibers may be performed using a drum rather than horizontally through a bath. In some cases, the drum depicted in FIG. 3 may be the same drum that is used during application of a sizing agent. Alternatively, the drum depicted in FIG. 3 may represent a first drum associated with the in-situ hollow fiber detection, and another drum may be utilized during application of the sizing agent.

Thus, FIG. 3 illustrates an example of another configuration for in-situ detection of hollow fiber formation. In the example of FIG. 3, individual glass fibers are rolled over a drum that has liquid cascading over it, the liquid having with a refractive index that substantially matches the refractive index of the glass. As in the example of FIG. 2, in the event that one or more of the individual glass fibers includes a hollow portion, the index of refraction of the air inside the fiber(s) will be different than that of the glass and the index-matching material. The optical component(s) may detect such light scattering, and the location(s) may be stored as glass fiber defect data for subsequent removal.

Figure 4:
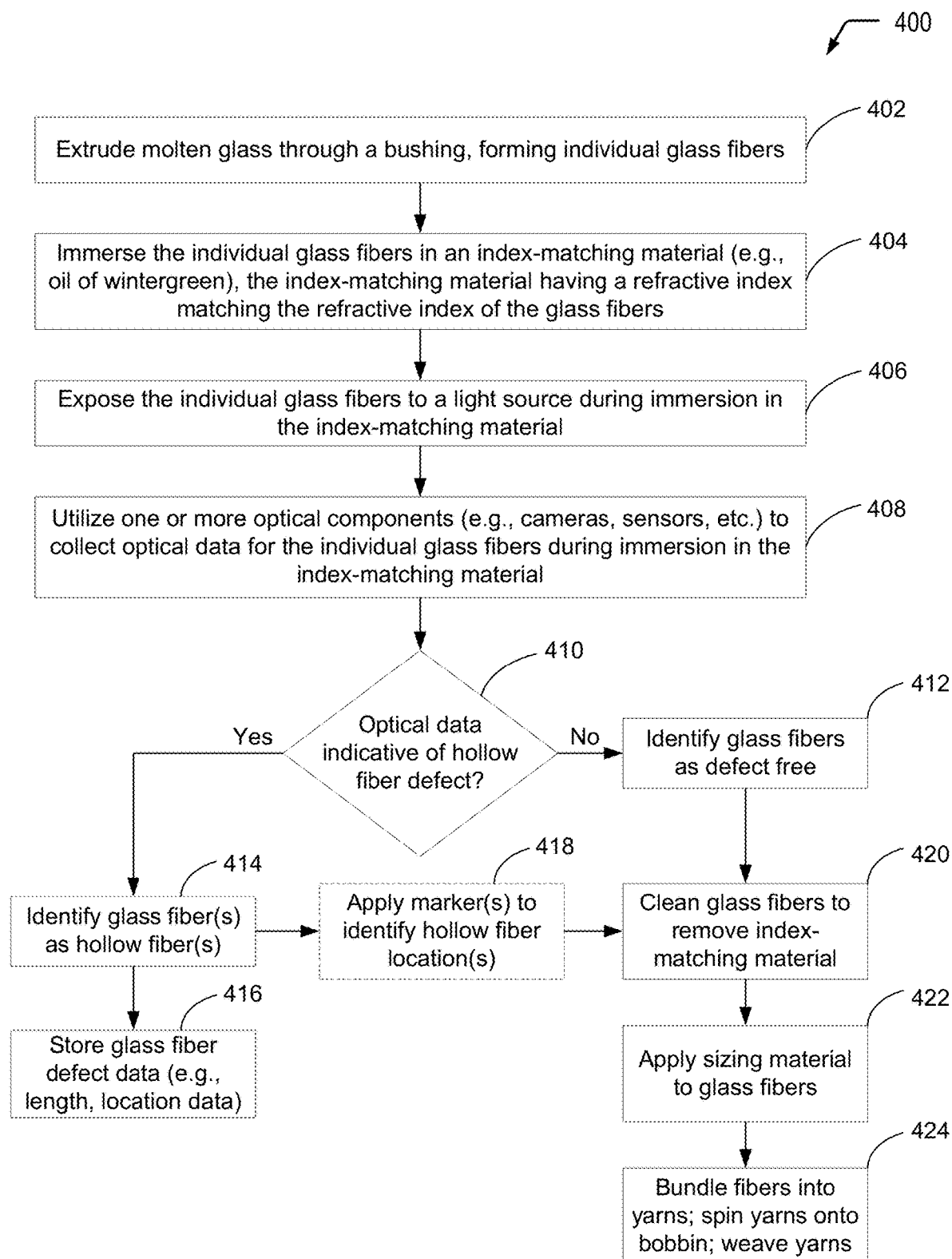
FIG. 4 is a flow diagram showing a particular embodiment of a process of in-situ detection of hollow fiber formation.

Referring to FIG. 4, a flow diagram depicts an example of a process 400 of in-situ detection of hollow fiber formation. In FIG. 4, prior to bundling of individual glass fibers (after the individual glass fibers leave the furnace), the individual glass fibers may be immersed in a material having an index of refraction that matches the index of refraction of the glass. While the individual glass fibers are immersed in the index-matching material, a light source may be used to illuminate hollow filaments that may be present in the individual glass fibers. The index of refraction of the immersion liquid matches that of the glass, resulting in light refraction only in locations where air is trapped in the glass fiber. Data associated with the locations of the hollow filaments may be stored. As described further herein with respect to FIG. 5, such glass fiber defect location data may be subsequently utilized for removal of sections of a woven glass cloth that include the hollow filaments. Selective removal of defective sections of the woven glass cloth may reduce a likelihood of circuit failure that may be associated with hollow filaments.

The process 400 includes extruding molten glass through a bushing to form individual glass fibers, at 402. For example, referring to FIG. 1, the molten glass 112 may be extruded through the bushing 120 to form the individual glass fibers 130. The individual glass fibers 130 depicted in the in-situ hollow fiber detection area 104 of FIG. 1 may correspond to the individual glass fibers illustrated in FIGS. 2 and 3.

The process 400 includes immersing the individual glass fibers in an index-matching material, at 404. The index-matching material has a refractive index that matches the refractive index of the glass fibers. For example, referring to FIG. 1, the individual glass fibers 130 may be immersed in an index-matching material in the in-situ hollow fiber detection area 104. As an example, referring to FIG. 2, immersion of the individual glass fibers 130 may include submerging the glass fibers 130 in the bath 206 that includes the index-matching material 208. As another example, referring to FIG. 3, immersion of the individual glass fibers 130 in the index-matching material 208 may include the individual glass fibers being rolled over a drum that has liquid cascading over the drum.

The process 400 includes exposing the individual glass fibers to a light source during immersion in the index-matching material, at 406. For example, referring to FIG. 1, the individual glass fibers 130 may be exposed to a light source (not shown in FIG. 1) while the individual glass fibers 130 are immersed in the index-matching material in the in-situ hollow fiber detection area 104. As an example, referring to FIG. 2, the glass fibers 130 may be exposed to the light source 202 while the glass fibers 130 are submerged in the bath 206 that includes the index-matching material 208. As another example, referring to FIG. 3, the glass fibers may be exposed to the light source while the individual glass fibers are being rolled over the drum that has liquid cascading over the drum.

The process 400 includes utilizing one or more optical components to collect optical data for the individual glass fibers during immersion in the index-matching material, at 408. For example, while not shown in FIG. 1, optical components (e.g., one or cameras or other optical sensors) may be utilized to collect optical data for the individual glass fibers 130 while the glass fibers 130 pass through the in-situ hollow fiber detection area 104. As an example, referring to FIG. 2, the optical component(s) 204 may be used to collect optical data 230 for the individual glass fibers 130 while the glass fibers 130 are submerged in the bath 206 that includes the index-matching material 208. As another example, referring to FIG. 3, optical data for the glass fibers may be collected while the individual glass fibers are being rolled over the drum that has liquid cascading over the drum.

The process 400 includes determining whether the optical data is indicative of a hollow fiber defect, at 410. For example, referring to FIG. 1, the determination of whether the individual glass fibers 130 include hollow fibers may be determined in the in-situ hollow fiber detection area 104. As an example, referring to FIG. 2, the computing device 210 may utilize the hollow fiber identification component 216 to determine based on the optical data 230 received from the optical component(s) 204 whether one or more of the glass fibers 130 includes hollow fibers. As another example, while not shown in the example of FIG. 3 where a drum is utilized to immerse the glass fibers in the index-matching material, similar operations may be performed to those described with respect to FIG. 2.

When the optical data is not indicative of a hollow fiber defect, the process 400 proceeds to identify the glass fiber(s) as defect free, at 412. When the optical data is indicative of a hollow fiber defect, the process 400 proceeds to 414, where the glass fiber(s) are identified as hollow fiber(s).

After identification of the glass fiber(s) as hollow fiber(s), at 414, the process 400 includes storing glass fiber defect data, at 416. For example, referring to FIG. 2, based on the optical data 230 received from the optical component(s) 204, the computing device 210 may store the glass fiber defect data 220. As another example, while not shown in the example of FIG. 3 where a drum is utilized to immerse the glass fibers in the index-matching material, similar operations may be performed to those described with respect to FIG. 2.

FIG. 4 illustrates that, in some cases, the process 400 may include applying one or more markers to identify hollow fiber location(s), at 418. As described further herein, such markers may make it easier for subsequent removal of defective sections of woven glass cloth (e.g., for formation of a prepreg material for a printed circuit board).

The process 400 may proceed to 420, where the glass fibers may be cleaned to remove the index-matching material. After removal of the index-matching material, the process 400 may include applying sizing material to the glass fibers, at 422. The process 400 further includes, at 424, bundling the fibers into yarns, spinning the yarns onto a bobbin, and weaving the yarns into glass cloths.

Thus, FIG. 4 illustrates an example of a process of in-situ detection of hollow fiber formation. As described further herein, the glass fiber defect data collected according to the process depicted in FIG. 4 may be utilized for subsequent removal of selected portions of glass cloth that include hollow fiber defect(s) in order to reduce a likelihood of printed circuit board failures associated with the presence of hollow fibers.

Figure 5:
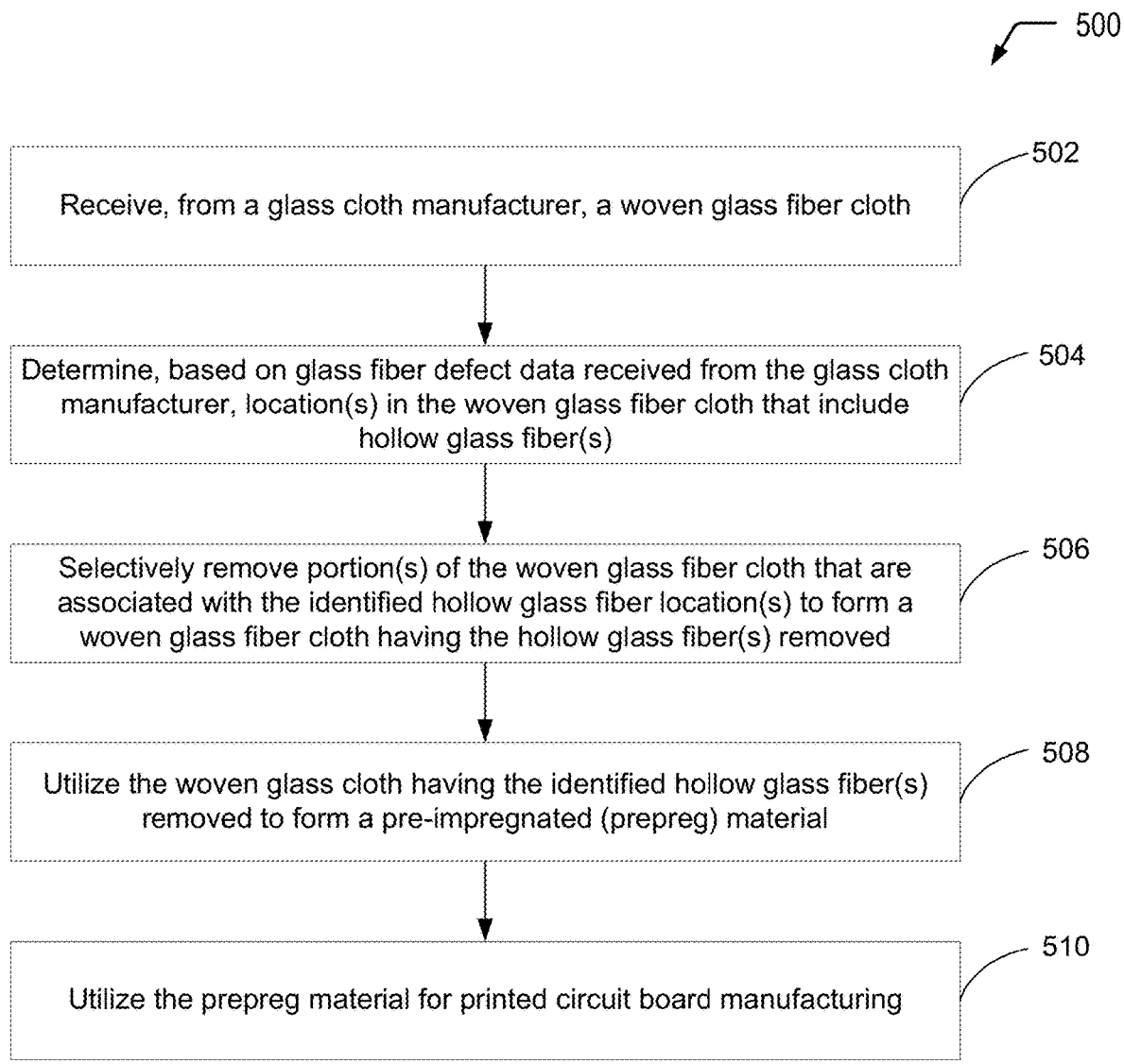
FIG. 5 is a flow diagram showing a particular embodiment of a process of utilizing glass fiber defect data collected by a glass cloth manufacturer via in-situ detection of hollow fiber formation to selectively remove defective portions of a woven glass cloth that include hollow glass fibers.

FIG. 5 is a flow diagram showing a particular embodiment of a process 500 of utilizing glass fiber defect data collected by a glass cloth manufacturer via in-situ detection of hollow fiber formation to selectively remove defective portions of a woven glass cloth that include hollow glass fibers.

The process 500 includes receiving, from a glass cloth manufacturer, a woven glass fiber cloth, at 502. For example, the woven glass fiber cloth may be manufactured according to the process depicted in FIG. 1.

The process 500 includes determining, based on glass fiber defect data received from the glass cloth manufacturer, location(s) in the woven glass fiber cloth that include hollow glass fiber(s), at 504. For example, the glass fiber defect data may be obtained according to the processes described herein with respect to FIGS. 2 and 3.

The process 500 includes selectively removing portion(s) of the woven glass fiber cloth that are associated with the identified hollow glass fiber location(s) to form a woven glass cloth having the identified hollow glass fiber(s) removed, at 506.

The process 500 includes utilizing the woven glass cloth having the identified hollow glass fiber(s) removed to form a pre-impregnated (prepreg) material, at 508. The process 500 further includes utilizing the prepreg material for printed circuit board manufacturing, at 510.

Thus, FIG. 5 illustrates an example of a process of utilizing glass fiber defect data collected by a glass cloth manufacturer via in-situ detection of hollow fiber formation to selectively remove defective portions of a woven glass cloth that include hollow glass fibers. As described further herein, removal of selected portions of glass cloth that include hollow fiber defect(s) may reduce a likelihood of printed circuit board failures associated with the presence of hollow fibers.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of in-situ detection of hollow fiber formation, the process comprising:
    immersing a plurality of individual glass fibers in an index-matching material by rolling the glass fibers over a drum while the index-matching material is cascaded over the drum, the index-matching material having a first refractive index that substantially matches a second refractive index of the glass fibers;
    exposing the individual glass fibers to a light source during immersion in the index-matching material;
    utilizing one or more optical components to collect optical data for the individual glass fibers during immersion in the index-matching material; and
    determining, based on the optical data, that a particular glass fiber of the plurality of individual glass fibers includes a hollow portion.

2. The process of claim 1, further comprising removing the index-matching material from the glass fibers before application of a sizing agent that is different from the index-matching material.

3. The process of claim 1, wherein the drum corresponds to a first drum that is different from a second drum that is used during subsequent application of a sizing agent to the glass fibers.

4. The process of claim 1, further comprising storing glass fiber defect data associated with the hollow portion of the particular glass fiber.

5. The process of claim 4, wherein the glass fiber defect data identifies a portion of a woven glass cloth that is formed from the plurality of individual glass fibers that includes the hollow portion of the particular glass fiber.

6. The process of claim 5, further comprising providing the glass fiber defect data to a manufacturer, the manufacturer to utilize the glass fiber defect data for selective removal of the portion of the woven glass cloth.

7. The process of claim 6, wherein the manufacturer includes a pre-impregnated (prepreg) material manufacturer, the selective removal of the portion of the woven glass cloth to prevent conductive anodic filament (CAF) formation associated with the presence of hollow glass filaments in a printed circuit board.

8. The process of claim 1, wherein the index-matching material includes oil of wintergreen.

9. An apparatus for in-situ detection of hollow fiber formation, the apparatus comprising:
    an immersion component to immerse a plurality of individual glass fibers in an index-matching material by rolling the glass fibers over a drum while the index-matching material is cascaded over the drum, the index-matching material having a first refractive index that substantially matches a second refractive index of the glass fibers;
    a light source to expose the individual glass fibers to light during immersion in the index-matching material;
    one or more optical components to collect optical data for the individual glass fibers during immersion in the index-matching material; and
    a hollow fiber identification component to determine, based on the optical data, that a particular glass fiber of the plurality of individual glass fibers includes a hollow portion.

10. The apparatus of claim 9, further comprising an index-matching material removal component to remove the index-matching material from the glass fibers after the immersion and before application of a sizing agent that is different from the index-matching material.

11. The apparatus of claim 9, wherein the drum corresponds to a first drum that is different from a second drum that is used during subsequent application of a sizing agent that is different from the index-matching material.

12. The apparatus of claim 9, wherein the index-matching material includes oil of wintergreen.

13. A process of in-situ detection of hollow fiber formation, the process comprising:
    prior to application of a sizing agent, immersing a plurality of individual glass fibers in an index-matching material that is different from the sizing agent, the index-matching material having a first refractive index that substantially matches a second refractive index of the glass fibers;
    exposing the individual glass fibers to a light source during immersion in the index-matching material;
    utilizing one or more optical components to collect optical data for the individual glass fibers during immersion in the index-matching material;
    determining, based on the optical data, that a particular glass fiber of the plurality of individual glass fibers includes a hollow portion; and
    storing glass fiber defect data associated with the hollow portion of the particular glass fiber.

14. The process of claim 13, wherein the individual glass fibers are immersed in the index-matching material by rolling the glass fibers over a drum while the index-matching material is cascaded over the drum.

15. The process of claim 14, wherein the drum corresponds to a first drum that is different from a second drum that is used during subsequent application of a sizing agent that is different from the index-matching material.

16. The process of claim 13, further comprising applying one or more markers to identify a defective section of the particular glass fiber that is associated with the hollow portion, the one or more markers to enable selective removal of the defective section to prevent conductive anodic filament (CAF) formation associated with the presence of hollow glass filaments.

17. The process of claim 13, further comprising:
    removing the index-matching material from the plurality of individual glass fibers after the immersion;
    applying the sizing agent to the plurality of individual glass fibers;
    forming a glass strand that includes the plurality of individual glass fibers; and
    forming a woven glass cloth that includes the glass strand, the glass fiber defect data identifying a portion of the woven glass cloth that includes the hollow portion of the particular glass fiber.

18. The process of claim 13, further comprising providing the glass fiber defect data to a manufacturer, the manufacturer to utilize the glass fiber defect data for selective removal of the portion of the woven glass cloth.

19. The process of claim 18, wherein the manufacturer forms a pre-impregnated (prepreg) material, the selective removal of the portion of the woven glass cloth to prevent conductive anodic filament (CAF) formation associated with the presence of hollow glass filaments in a printed circuit board formed from the prepreg material.

20. The process of claim 13, wherein the index-matching material includes oil of wintergreen.

\* \* \* \* \*